United States Patent [19]

Odenwälder et al.

[11] 4,171,223
[45] Oct. 16, 1979

[54] LIGHT-SENSITIVE COLOR PHOTOGRAPHIC MATERIAL

[75] Inventors: Heinrich Odenwälder, Cologne; Walter Püschel; Erwin Ranz, both of Leverkusen, all of Fed. Rep. of Germany

[73] Assignee: AGFA-Gevaert, A.G., Leverkusen, Fed. Rep. of Germany

[21] Appl. No.: 918,390

[22] Filed: Jun. 23, 1978

[30] Foreign Application Priority Data

Jun. 29, 1977 [DE] Fed. Rep. of Germany ....... 2729213

[51] Int. Cl.$^2$ ................. G03C 1/48; G03C 5/30; G03C 1/40; G03C 1/06
[52] U.S. Cl. ................. 96/76 R; 96/66.3; 96/95; 96/100 R
[58] Field of Search ........... 96/56.3, 100 R, 66.3, 96/95, 76 R, 56

[56] References Cited

U.S. PATENT DOCUMENTS

| | | | |
|---|---|---|---|
| 3,620,745 | 11/1971 | Seymour | 96/100 R |
| 3,841,880 | 10/1974 | Kertel | 96/56.3 |

*Primary Examiner*—Richard L. Shilling

[57] ABSTRACT

Non-diffusible silver halide development inhibitor releasing thioether compounds in which a color development does not give rise to a substantial formation of permanent dyes are 1,2,5′-Δ$^2$-thiadiazoline-1,1-dioxide derivatives of the following formula or its tautomeric (Δ$^3$) form:

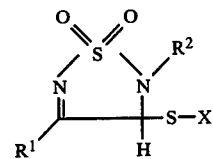

I in which
X represents an aliphatic, aromatic or heterocyclic group such that when it is split off together with the sulphur atom of the thioether bridge, it forms a diffusible mercapto compound capable of inhibiting the development of the silver halide;
R$^1$ represents hydrogen, alkyl, aryl or a heterocyclic group and
R$^2$ represents hydrogen, alkyl, aryl, a heterocyclic group or preferably acyl.

2 Claims, No Drawings

LIGHT-SENSITIVE COLOR PHOTOGRAPHIC MATERIAL

This invention relates to a colour photographic material containing compounds which react with the oxidation products of colour developer compounds to release development inhibiting substances.

It is known to incorporate in colour photographic materials compounds which release development inhibitors when they react with colour developer oxidation products. Compounds of this kind are, for example, the so-called DIR couplers (DIR=Development Inhibitor Releasing) described in U.S. Pat. No. 3,227,554. These compounds are colour couplers which contain, in the coupling position, a thioether substituent which is split off as a diffusible mercapto compound in the process of colour coupling, which mercapto compound has development inhibiting properties and is therefore capable of influencing the subsequent development of the silver halide.

The use of such DIR couplers improves the properties of colour photographic materials in several respects. They can be used to control the graininess, sharpness and gradation, whereby the colour reproduction can be substantially improved. Reference may be made in this connection to the article "Development Inhibitor Releasing (DIR Couplers in Colour Photography", in Photographic Science and Engineering 13, 74 (1969).

The above-mentioned DIR couplers inevitably give rise to a dye together with the released development inhibitor. It is therefore necessary to make a careful choice of the DIR coupler used in order to ensure a good colour balance in the colour photographic material. In particular, a given DIR coupler cannot be used in all of the colour-producing and non-colour producing layers of a colour photographic multi-layer material because the dye produced from the coupler generally only corresponds in its colour to the image dye of one layer and would increase the unwanted side densities of the partial colour images formed in the two other layers.

These disadvantages do not arise if, instead of the DIR couplers, there are used compounds which react with colour developer oxidation products to release diffusible development inhibitors without at the same time substantially contributing to the formation of a dye. Such compounds, which may be referred to as DIR compounds to distinguish them from the above-mentioned DIR couplers, have been described, for example, in U.S. Pat. No. 3,632,345. The compounds described therein are mainly acetophenone derivatives which carry a thioether substituent in the ω-position. This substituent is obviously split off in the reaction with the oxidation products of colour developer compounds. Another group of development inhibitor releasing compounds which also do not give rise to dyes has been described in German Offenlegungsschrift No. 2,359,295. These DIR compounds are cycloalkanones which carry a thioether substituent in the α-position to the keto group. Other DIR compounds have been described in German Offenlegungsschriften Nos. 2,362,752; 2,405,442; 2,448,063 and 2,529,350. It has been found, however, that under certain processing conditions the known DIR compounds are either too unstable or insufficiently reactive. If they are too unstable the development inhibitor is not released imagewise, so that there is a general reduction in sensitivity. If, on the other hand, they are not sufficiently reactive, the inhibitor is split off two slowly and is therefore unable to intervene in the development process to a sufficient extent.

It is an object of the present invention to provide new compounds which react with colour developer oxidation products to release development inhibiting substances without at the same time giving rise to substantial production of dyes harmful to the formation of the colour image and which are both sufficiently reactive and sufficiently stable.

There has now been found a new class of compounds which manifest the DIR effect described above to a remarkable degree and which may be considered to belong to the group of DIR compounds. These new compounds are derivatives of 1, 2, 5-$\Delta^2$-thiadiazoline-1,1-dioxide which carry a thioether group in the 4-position of the above-mentioned heterocyclic compound.

The present invention relates to a colour photographic material which contains a preferably non-diffusible thioether compound in at least one silver halide emulsion layer or in a light insensitive layer of binder associated therewith, which thioether compound reacts with the oxidation product of a colour developer compound containing a primary aromatic amino group to release a diffusible substance capable of inhibiting the development of the silver halide.

The colour photographic material according to the present invention contains a DIR compound represented by the following formula I or its tautomeric ($\Delta^3$) form:

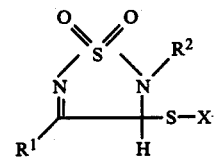

in which
X represents an aliphatic, aromatic or heterocyclic group such that when it is split off together with the sulphur atom of the thioether bridge, it forms a diffusible mercapto compound capable of inhibiting the development of the silver halide;
$R^1$ represents hydrogen, alkyl, aryl or a heterocyclic group and
$R^2$ represents hydrogen, alkyl, aryl, a heterocyclic group or preferably acyl.

The above-mentioned alkyl groups which may be represented by $R^1$ and $R^2$ may, in particular, contain up to 18 carbon atoms and may be further substituted, for example by halogen, hydroxyl, carboxyl, sulpho, aryl, alkoxy, aroxy, a heterocyclic group, amino or acylamino.

The above-mentioned aryl groups include in particular phenyl and naphthyl groups, which may in turn carry substituents such as halogen, alkyl, alkoxy, alkylthio, carboxyl, sulpho, a heterocyclic group, amino, acylamino or acyl.

It should be particularly mentioned that the above-mentioned heterocyclic groups may be thienyl or furyl, which may in turn be substituted.

Acyl groups, which $R^2$ may represent or which may be present as substituents, for example on an aryl group represented by $R^1$ or $R^2$, are derived from aliphatic or aromatic carboxylic acids or sulphonic acids, including carbonic acid monoesters, carbamic acids and sulphamic acids. The following are examples of such acyl groups: acetyl, benzoyl, dodecanoyl, hexadecanoyl, dodecyloxycarbonyl, N-phenyl-carbamoyl, N-Hexadecylcarbamoyl and phenyloxycarbonyl.

Examples of aliphatic groups which X may represent are the following:

—CH₂—COOH and

—CH₂—CH—NH₂
       |
       COOH

Examples of aromatic groups which X may represent also include substituted phenyl and naphthyl groups such as phenyl itself, carboxyphenyl and nitrophenyl.

The following are examples of heterocyclic groups which X may represent:

Tetrazolyl, such as 1-phenyltetrazolyl, 1-nitrophenyltetrazolyl or 1-naphthyltetrazolyl;
Triazolyl, such as 1-phenyl-1,2,4-triazolyl;
Thiadiazolyl, such as 2-phenylamino-1,3,4-thiadiazolyl;
Oxadiazolyl;
Thiazolyl, including benzothiazolyl and naphthothiazolyl;
Oxazolyl, including benzoxazolyl and naphthoxazolyl, for example 7-sulphonaphtho[2,3-d]oxazolyl;
Pyrimidyl, such as 4-methyl-6-aminopyrimidyl or 4-methyl-6-hydroxypyrimidyl; or
Triazinyl, such as thiadiazolotriazinyl.

One of the substituents R¹ and R² preferably contains a group which confers resistance to diffusion, preferably a long chain alkyl group. Groups which may be regarded as conferring diffusion resistance are those which make it possible for the compounds according to the invention to be incorporated in a diffusion fast form in the hydrophilic colloids normally used in photographic materials. Organic groups are particularly suitable for this purpose, and these may generally contain straight or branched chain aliphatic groups and may also contain carbocyclic or heterocyclic aromatic groups. The aliphatic portion of these groups generally contains from 8 to 20 carbon atoms. These groups are attached to the remainder of the molecule either directly or indirectly, e.g. by way of one of the following groups: —CONH—; —SO₂NH—; —CO—; —SO₂—; —NR—, in which R represents hydrogen or alkyl; —O—; or —S—.

The diffusion resistance-conferring group may, in addition, contain water solubilising groups such as sulpho groups or carboxyl groups, and these may also be present in the anionic form. Since the diffusion properties depend on the molecular size of the compound as a whole, it is sufficient in some cases, e.g. if the whole molecule used is large enough, to use only relatively short chain groups for conferring diffusion resistance, for example cyclopentyl or tertiary amyl groups.

Some examples of compounds to be used according to the invention are indicated below:

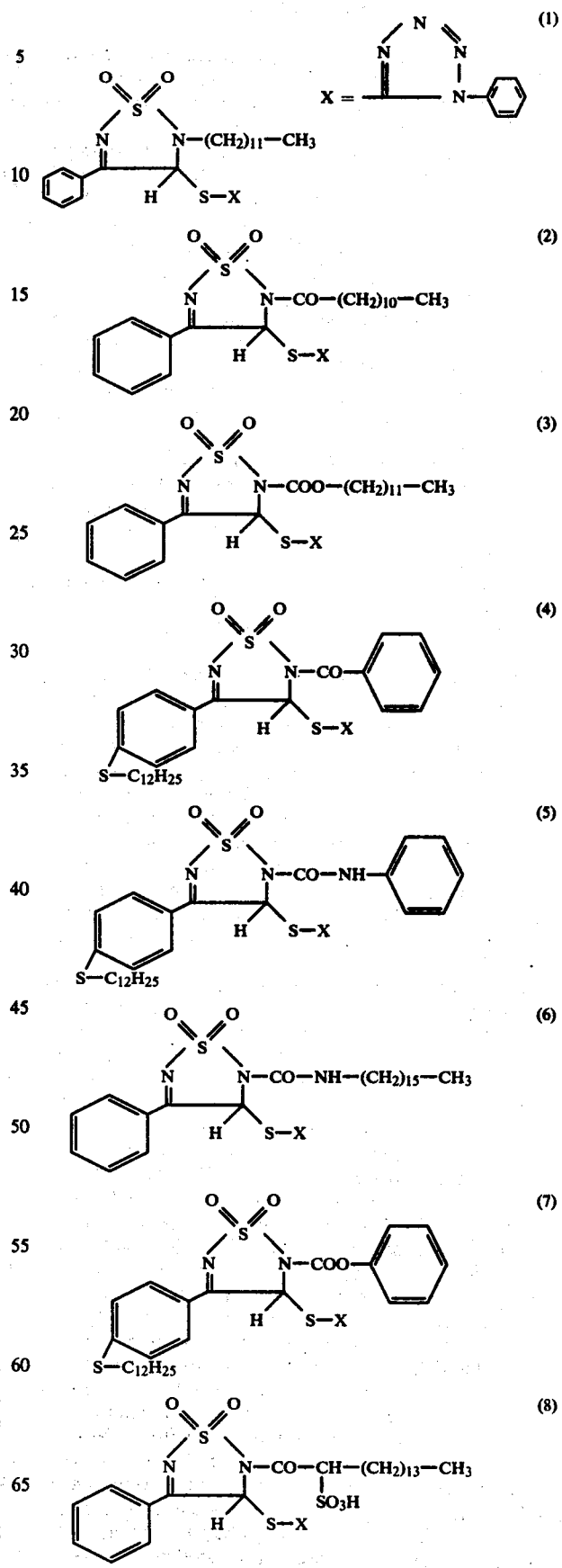

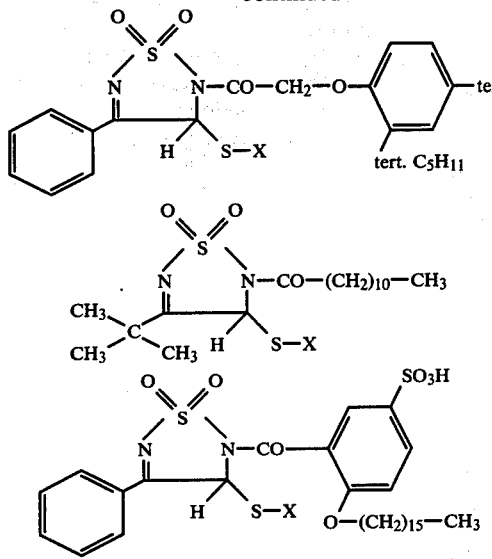

Introduction of the inhibitor group —SX into the 1,2,5-thiadiazoline-1,1-dioxide ring may be carried out by generally known chemical methods, for example by halogenation and exchange of the halogen by the group SX or by reaction with the sulphenyl halide hal—S—X or the disulphide X—S—S—X.

EXAMPLES OF PREPARATION

Compound No. 1/First Stage 81 g of dodecylamine and 42 g of sulphuryl diamide in a mixture of 50 ml of water and 20 ml of dimethoxyethane were heated under reflux for 4.5 hours. The mixture was poured, with stirring, into 1 liter of water to which 50 ml of glacial acetic acid had been added. The precipitate was suction filtered and recrystallized from methanol. 59 g of N-dodecylsulphuryldiamide which melts between 95° C. and 105° C. were obtained.

Second Stage 10.5 g of the compound obtained according to Stage 1 and 7.15 g of 1-acetoxy-2-phenyl-ethanone in 50 ml of absolute ethanol were vigorously stirred with introduction of hydrogen chloride gas until the temperature of the reaction mixture reached 70° C. The addition of hydrogen chloride was then stopped and the mixture was heated under reflux for 30 minutes and then poured out into about 200 ml of water. The precipitate was suction filtered and stirred up, first with about 300 ml of water and then with about 200 ml of methanol. After suction filtration and washing with 50 ml of methanol, there were obtained 5.7 g of 5-dodecyl-3-phenyl-1,2,-5-$\Delta^2$-thiadiazoline-1,1-dioxide, melting point 115.5° to 116° C.

Third Stage 1.2 g of sodium acetate sicc. were added to 3.65 g of the compound obtained according to Stage 2 and 3.5 g of di-(1-phenyl-5-tetrazolyl)-disulphide in 70 ml of ethanol. The mixture was then stirred for 10 minutes at 70° C. and thereafter for 1 hour at room temperature and the resulting precipitate was suction filtered and washed with methanol. After precipitation from ethyl acetate/methanol there were obtained 4.6 g of 5-dodecyl-3-phenyl-4-(1-phenyl-5-tetrazolylthio)-1,2,5-$\Delta^2$-thiadiazoline-1,1-dioxide, melting point 123° to 123.5° C.

Compound No. 2/First Stage 160.2 g of 1-acetoxy-2-phenyl-ethanone and 86.4 g of sulphuryl diamide in 900 ml of absolute ethanol were vigorously stirred with the introduction of hydrogen chloride gas until the temperature of the reaction mixture reached 50° C. and the components had dissolved. The addition of hydrogen chloride was then stopped and the mixture was heated under reflux for 1 hour and then poured into 2 liters of water. The precipitate was suction filtered, washed neutral with water and then stirred up with 400 ml of isopropanol. After suction filtration with ice cold isopropanol, there were obtained 132.2 g of 3-phenyl-1,2,5-$\Delta^2$-thiadiazoline-1,1-dioxide, melting point 152°–153° C.

Second Stage 6 g of lauric acid chloride were added with stirring to 5 g of the reaction product of Stage 1 in 30 ml of acetone. 3.5 ml of triethylamine were added dropwise within 3 minutes. After 1 hour, 60 ml of methanol were added, the reaction mixture was cooled in an ice bath and the precipitate was suction filtered and washed with methanol. 5.9 g of 5-lauroyl-3-phenyl-1,2,5-$\Delta^2$-thiadiazoline-1,1-dioxide, melting point 135°–136° C. were obtained.

Third Stage 1.2 g of sodium acetate sicc were added to 4.9 g of the compound obtained according to Stage 2 and 4.5 g of di-(1-phenyl-5-tetrazolyl)-disulphide in 80 ml of ethanol and the mixture was heated to 70° C. for 10 minutes with stirring. Stirring was then continued at room temperature for 1 hour and the mixture was then cooled in an ice bath. The resulting precipitate was suction filtered and washed with methanol. The crude product obtained was dissolved hot in 30 ml of ethyl acetate and again precipitated by the addition of 70 ml of methanol. 6.5 g of 5-lauroyl-3-phenyl-4-(1-phenyl-5-tetrazolylthio)-1,2,5-$\Delta^2$-thiadiazoline-1,1-dioxide, melting point 158° C. were obtained.

Compounds Nos. 3 to 11 may be obtained by a method similar to that employed for Compound No. 2 if differently 3-substituted 1,2,5-$\Delta^2$-thiadiazoline-1,1-dioxides are similarly used in Stage 2 and/or if lauroyl chloride is replaced by other carboxylic acid chlorides or by chlorocarbonic acid esters or isocyanates and the process is then continued as in Stage 3.

The compounds according to the invention are comparable in the following respect with the known DIR couplers described in U.S. Pat. No. 3,227,554: Like these known DIR couplers, they constitute non-diffusible thioether compounds which react with colour developer oxidation products to release a diffusible mercaptan which inhibits the development of the silver halide. However, in contrast to the known DIR couplers, the compounds according to the invention generally give rise to colourless or only slightly coloured reaction products in the reaction with the oxidation products of colour developer substances, so that these reaction products do not impair the finished colour image. The compounds according to the invention may therefore be referred to as DIR compounds in contrast to the known DIR couplers. According to U.S. Pat. No. 3,148,062, DIR couplers are sub-divided into those in which the group which is released already has an inhibitory action before the coupling reaction and those in which the inhibitory action comes into existence only when a molecular group is released from the coupling position. In the latter case, the inhibitor is said to be non-preformed.

In accordance with this terminology, the compounds according to the invention may be described as non-diffusible compounds which react with colour developer oxidation products to release a diffusible, non-preformed development inhibitor.

Compared with the compounds according to U.S. Pat. No. 3,632,345 and German Offenlegungsschrift No. 2,359,295, the compounds according to the invention are distinguished by their enhanced reactivity, which is particularly advantageous when development is carried out at a relatively low pH, e.g. at pH 10 to 11. The DIR compounds according to the invention are still sufficiently active under these conditions.

The DIR compounds according to the invention are particularly suitable for use in colour photographic multilayered materials of the kind in which the imagewise exposed silver halide is developed by conventional colour developers, e.g. by the usual aromatic compounds based on p-phenylene diamine and containing at least one primary amino group.

The following are examples of suitable colour developers: N,N-dimethyl-p-phenylenediamine; N,N-diethyl-p-phenylenediamine; monomethyl-p-phenylenediamine; 2-amino-5-diethylaminotoluene; N-butyl-N-$\omega$-sulphobutyl-p-phenylenediamine; 2-amino-5-(N-ethyl-N-$\beta$-methanesulphonamidoethyl-amino)-toluene; N-ethyl-N-$\beta$-hydroxyethyl-p-phenylenediamine; N,N-bis-($\beta$-hydroxyethyl)-p-phenylenediamine and 2-amino-5-(N-ethyl-N-$\beta$-hydroxyethylamino)-toluene.

Other suitable colour developers have been described, for example, in J.A.C.S. 73, 3100 (1951). The developer compounds are normally contained in an alkaline development bath used for treating the imagewise exposed colour photographic material but they may also be incorporated in one or more layers of the photographic material. In the latter case, the developer compounds may contain diffusion resistance conferring groups and they may be contained in a layer which also contains a diffusion resistant colour coupler or a diffusion resistant colour-providing compound, for example as described in U.S. Pat. No. 3,705,035. In that case, all that is necessary for development is an alkaline activator solution containing an auxiliary developer, for example phenidone. The oxidation product of the colour developer produced on development reacts with the non-diffusible colour coupler to form a non-diffusible image dye or it reacts with the non-diffusible colour-providing compound to form diffusible dyes in imagewise distribution, which may then be transferred to an image receiving layer. At the same time, the oxidation product of the colour developer reacts with the non-diffusible DIR compounds according to the invention, which are also present, to release diffusible inhibitor molecules while from the remainder of the molecule of the DIR compound there is generally formed only a colourless compound or an impermanent dye, that means a dye which is substantially decolourised during the photographic processing so that it does not contribute in any substantial amount to the final colour image.

The colour photographic multi-layered material according to the invention contains a DIR compound in at least one of its layers. This compound may be incorporated in a light sensitive silver halide emulsion layer or in a hydrophilic layer of binder which is associated with such a light sensitive silver halide emulsion layer and need not itself be light sensitive. By "associated layer" is meant in this context a layer which is situated in such a spatial relationship to the light sensitive silver halide emulsion layer, that, when development of the siler halide emulsion layer takes place, significant quantities of colour developer oxidation products occur in it due to diffusion from the light sensitive silver halide emulsion layer. The concentration of DIR compound according to the invention in any given layer may vary within wide limits, e.g. between $1 \times 10^{-3}$ and $300 \times 10^{-3}$ mol per kg of silver halide while in associated layers of binder it may occur e.g. at concentrations of between $0.05 \times 10^{-3}$ and $1 \times 10^{-3}$ mol per g of binder. The concentration depends in each case on the purpose for which the compound is to be used, the particular silver halide emulsion and on whether the DIR compound is contained in a silver halide emulsion layer or in a light insensitive binder layer. The upper limit generally lies at concentration levels at which colour couplers are also used in photographic layers but the observance of such a limit is not critical since the DIR compounds according to the invention as such make only an insigificant contribution to the colour image.

The colour developer oxidation products are taken up by the reaction with the compounds according to the invention to form colourless or only slightly coloured products and are in this way withdrawn from any further colour forming reaction. The compounds according to the invention are therefore comparable in this respect to the known white couplers such as those described, for example, in U.S. Pat. No. 2,998,314. On the other hand, in this reaction, a diffusible mercapto compound is released, which is capable of inhibiting any further development of the silver halide. The inhibitory action may take place both in the layer which contains the compounds according to the invention, if this layer contains developable silver halide, and in adjacent silver halide emulsion layers into which the released inhibitor is capable of diffusing. In this way, the compounds according to the invention can be used to control the development in each individual light sensitive silver halide emulsion layer in several aspects and, by making use of the vicinal effects made possible by the compounds according to the invention, it is also possible to influence the development of one silver halide emulsion layer by the results of imagewise development produced in another layer so that an overall improvement in graininess, sharpness and colour reproduction can be achieved.

The DIR compounds according to the invention may be combined with each other or with other known DIR compounds or DIR couplers in order to achieve special effects. German Offenlegungsschrift No. 2,509,722 should be particularly referred to in this connection.

The light sensitive silver halide emulsion layers of the photographic material according to the invention have differing spectral sensitivities and, with each of these layers, there is associated at least one non-diffusible compound to produce an image dye having a colour which is generally complementary to the spectral sensitivity. These compounds may be conventional colour couplers which are generally incorporated in the silver halide layers. Thus the red-sensitive layer, for example, contains a non-diffusible colour coupler to produce the cyan partial colour image, generally a coupler based on phenol or α-naphthol. The green sensitive layer contains at least one non-diffusible colour coupler for producing the magenta partial colour image, usually a colour coupler based on 5-pyrazolone or indazolone. Lastly, the blue sensitive layer contains at least one non-diffusible colour coupler for producing the yellow partial colour image, generally a colour coupler with an open chain ketomethylene group. Colour couplers of these kinds are known in large numbers and have been described in numerous patent specifications and other publications, for example in the publication "Farbkuppler" by W. Pelz in "Mitteilungen aus den Forschungslaboratorien der Agfa, Leverkusen/Munchen", Volume III, page 111 (1961.). The non-diffusible colour couplers may contain a releasable substituent in the coupling position so that they require only two equivalents of silver halide for colour formation in contrast to the usual 4-equivalent couplers. The colour couplers themselves are generally colourless but if the releasable substituent contains a chromophoric group, as in the known masking couplers, the colour couplers generally have a colour which is suitable for masking unwanted side densities of the image dye by the usual masking techniques. Image dyes produced from colour couplers are generally diffusion fast.

If one or more than one silver halide emulsion layer of the material according to the invention is formed as a double layer consisting of two partial layers which may have different sensitivities or different silver-coupler ratios, a measure which has been proposed for obtaining an improved sensitivity-graininess relationship, i.e. for increasing the sensitivity without coarsening the colour grain (e.g. German Pat. No. 1,121,470, U.S. Pat. No. 3,726,681 and German Offenlegungsschriften Nos. 2,322,165 and 2,416,982), one or both of these partial layers of a double layer according to the invention may contain one or more of the DIR compounds according to the invention.

The image dyes may first be produced in a diffusible form during development and only subsequently fixed by transfer to an image receiving layer, as is known from various dye diffusion transfer processes, e.g. according to U.S. Pat. Nos. 3,227,550; 3,628,952 and German Pat. No. 1,772,929. In such cases, the light sensitive silver halide emulsion is associated with colourless or coloured non-diffusible colour providing compounds which release diffusible dyes in imagewise distribution as a result of development. Such colour providing compounds are incorporated either with the silver halide emulsion layer or with an associated hydrophilic layer of binder which may, for example, contain development nuclei and may also contain a silver halide when is developable without exposure.

When conventional silver halide emulsions are used in combination with non-diffusible colour couplers or non-diffusible colour providing compounds, negative colour images are normally obtained. However, the DIR compounds according to the invention, as also the DIR couplers, may advantageously be employed in reversal processes to produce positive images, both in conventional reversal processes in which the photographic material is first subjected to a black and white development after imagewise exposure and then colour developed, after or during a reversal fogging treatment e.g. by a diffuse second exposure, and in those reversal processes in which reversal of the imagewise information in the photographic material occurs due to the presence of the DIR compounds according to the invention. Such reversal takes place if, for example, a silver halide emulsion layer which is capable of spontaneous development, i.e. development without exposure, and which contains a colour coupler or a colour providing compound is arranged adjacent to a conventional silver halide emulsion layer which contains a DIR compound. It will be clear that DIR couplers or DIR compounds used for such a procedure must be capable of releasing the inhibitor as rapidly as possible so that it will effect imagewise inhibition of development in the spontaneously developable layer.

The non-diffusible development inhibitor releasing compound used according to the invention are added to the light sensitive silver halide emulsions or other casting solutions by the usual, known methods. If the compounds are soluble in water or alkalis, they may be added to the emulsions in the form of aqueous solutions, to which water miscible organic solvents such as ethanol, acetone or dimethylformamide may be added. If the non-diffusible colour couplers, colour providing compounds and development inhibitor releasing compounds used are insoluble in water or alkalis, they may be emulsified in known manner, e.g. by mixing a solution of these compounds in a low boiling organic solvent directly with the silver halide emulsion or by mixing it first with an aqueous gelatine solution and then evaporating off the organic solvent. The resulting gelatine emulsion of the given compound is then mixed with the silver halide emulsion. When emulsifying such hydrophobic compounds, there may in addition be used so-called coupler solvents or oil formers. These are generally higher boiling organic compounds which enclose in the form of oily droplets the non-diffusible colour couplers and development inhibitor releasing compounds which are required to be emulsified in the silver halide emulsions. Reference may be made in this connection to, for example, U.S. Pat. Nos. 2,322,027; 3,689,271; 3,764,336 and 3,765, 897. If the compounds according to the invention are emulsified in the layers with the aid of such oil formers, the diffusion resistance-conferring groups in the compounds according to the invention need not be so efficient as is otherwise necessary. In such a case, relatively short alkyl groups, e.g. isoamyl groups, may occasionally be sufficient to prevent diffusion of the compounds according to the invention in the layers of the photographic material. Furthermore, aqueous dispersions of the DIR compounds according to the invention may be prepared and added to the given casting solutions. For this purpose, aqueous suspensions of the compounds are ground down to a fine particle size by vigorous stirring or by the addition of sharp edged sand and/or by means of ultra sound, optionally in the presence of a suitable hydrophilic binder such as gelatine.

The usual silver halide emulsions are suitable for the present invention. The silver halide contained in them may be silver chloride, silver bromide or mixtures thereof, and may have a small silver iodide content of up to 10 mol-%. They may be either conventional negative emulsions or direct positive emulsions, e.g. those which have a high sensitivity in the interior of the silver halide grains, for example the emulsions described in U.S. Pat. No. 2,592,250.

The binder used for the photographic layers is preferably gelatine but this may be partly or completely replaced by other natural or synthetic binders. Suitable natural binders include e.g. alginic acid and its derivatives, such as its salts, esters or amides; cellulose derivatives such as carboxymethyl-cellulose; alkyl celluloses such as hydroxyethyl cellulose; starch or its derivatives, such as its ethers or esters; or carrageenates. Examples of suitable synthetic binders include polyvinyl alcohol, partially saponified polyvinyl acetate, polyvinyl pyrrolidone and the like.

The emulsions may also be chemically sensitized, e.g. by the addition of sulphur compounds such as allyl isothiocyanate, allyl thiourea, sodium thiosulphate and the like at the stage of chemical ripening. Reducing agents may also be used as chemical sensitizers, e.g. the tin compounds described in Belgian Pat. Nos. 493,464 and 568,687, polyamines such as diethylene triamine, or aminomethane sulphinic acid derivatives, e.g. according to Belgian Pat. No. 547,323.

Noble metals such as gold, platinum, palladium, iridium, ruthenium or rhodium and compounds of these metals are also suitable chemical sensitizers. This method of chemical sensitization has been described in the article by R. Koslowsky, Z. Wiss. Phot. 46, 65 to 72 (1951).

The emulsions may also be sensitized with polyalkylene oxide derivatives, e.g. with a polyethylene oxide having a molecular weight of between 1000 and 20,000, or with condensation products of alkylene oxides and aliphatic alcohols, glycols, cyclic dehydration products of hexitols, alkyl-substituted phenols, aliphatic carboxylic acids, aliphatic amines, aliphatic diamines and amides. The condensation products have a molecular weight of at least 700, preferably more than 1,000. The sensitizers may, of course, also be combined in order to achieve special effects, as described in Belgian Pat. No. 537,278 and British Pat. No. 727,982.

The emulsions may also be spectrally sensitized, e.g. with the usual monomethine or polymethine dyes such as acid or basic cyanines, hemicyanines, streptocyanines, merocyanines, oxonols, hemioxonols or styryl dyes or with trinuclear or higher polynuclear methine dyes such as rhodacyanines or neocyanines. Sensitizers of this kind have been described, for example, in the work by F. M. Hamer "The Cyanine Dyes and Related Compounds" (1964), Interscience Publishers John Wiley and Sons.

The emulsions may contain the usual stabilisers, e.g. homopolar or salt-type compounds of mercury containing aromatic or heterocyclic rings, such as mercaptotriazoles, simple mercury salts, sulphonium-mercury double salts and other mercury compounds. Azaindenes are also suitable stabilizers, particularly tetra and pentaazaindenes, especially those which are substituted with hydroxyl or amino groups. Compounds of this type have been described in the article by Birr. Z. Wiss. Phot, 47, 2–27 ( 1952). Other suitable stabilizers include heterocyclic mercapto compounds, e.g. phenyl mercapto tetrazole, quaternary benzothiazole derivatives and benzotriazole.

The emulsions may also be hardened in the usual manner, for example with formaldehyde or halogen-substituted aldehydes which contain a carboxyl group, such as mucobromic acid, diketones, methane sulphonic acid esters, dialdehydes and vinyl sulphone compounds.

The photographic layers may also be hardened with epoxide hardeners, heterocyclic ethylene imine hardeners or acryloyl hardeners. Examples of such hardeners have been described e.g. in German Offenlegungsschrift No. 2,263,602 and in British Pat. No. 1,266,655. The layers may also be hardened by the process according to German Offenlegungsschrift No. 2,218,009 to produce colour photographic materials which are suitable for high temperature processing.

EXAMPLES

Structure of the light sensitive colour photographic material

The DIR compounds are preferably used in multi-layered materials such as those commonly used for the preparation of light sensitive negative or positive colour photographic materials.

The effect of the DIR compounds according to the invention will be illustrated by the example of two typical layer arrangements or partial layers for colour negative materials.

The layers are applied to a transparent layer in the sequence indicated. The quantities refer to one square meter in each case. The quantity of silver applied is given in terms of the corresponding quantity of silver nitrate.

Layer arrangement I

1. A less sensitive red sensitive layer, containing a red sensitized silver iodobromide emulsion (5 mol-% silver iodide) of 3.0 g of silver nitrate with 790 mg of a cyan coupler of the following formula:

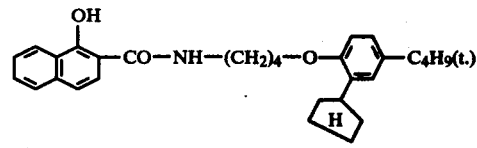

and 50 mg of masking coupler of the following formula:

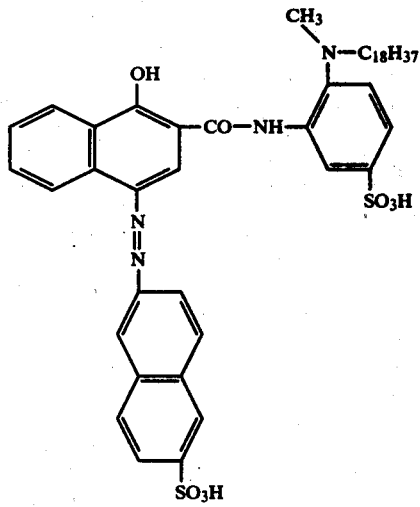

and 1.6 g of gelatine.
2. A high sensitivity red sensitive layer containing a red sensitized silver iodobromide emulsion (5 mol-% of silver iodide) of 2.0 g of silver nitrate with 250 mg of the cyan coupler of layer 1 and 1.0 g of gelatine and 25 mg of the masking coupler of layer 1.
3. An intermediate layer of 0.7 g of gelatine.
4. A less sensitive green sensitive layer containing a green sensitized mixture of a relatively high sensitivity silver iodobromide emulsion (5 mol-% of silver iodide) of 1.5 g of silver nitrate and a relatively insensitive silver iodobromide emulsion (% I) of 1.9 g of silver nitrate with 660 mg of a magenta coupler of the following formula:

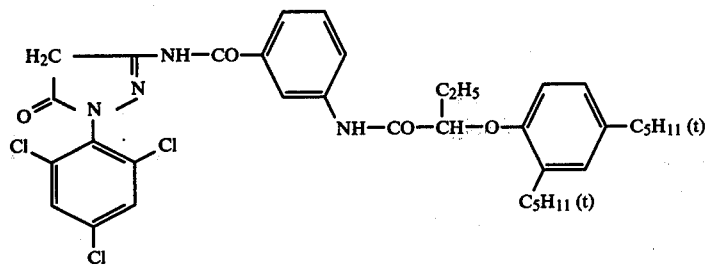

80 mg of a masking coupler of the following formula:

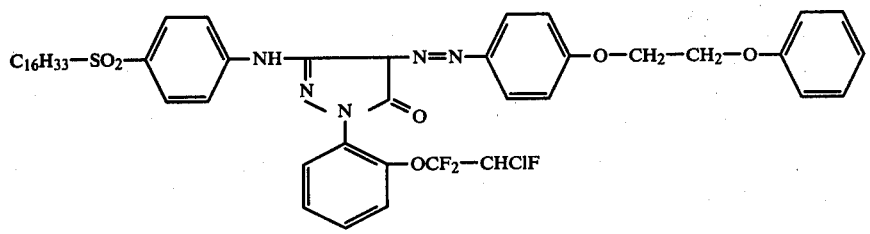

and 2.0 g of gelatine.

5. A high sensitivity green sensitive layer containing a green sensitized silver iodobromide emulsion (7 mol-% of silver iodide) of 2.8 g of silver nitrate with 170 mg of a magenta coupler of the following formula:

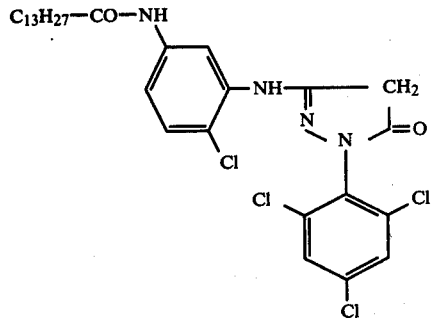

and 37 mg of a magenta coupler of the following formula:

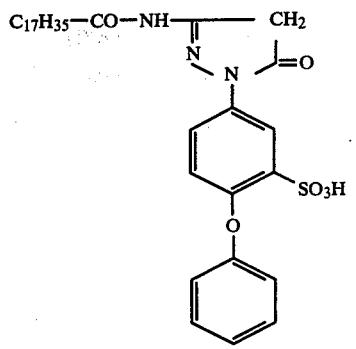

6. An intermediate layer containing 0.7 g of gelatine.
7. A yellow filter layer with colloidal silver for producing a yellow density of 0.8.
8. A blue sensitive layer containing a mixture of a sensitive silver iodobromide emulsion (9 mol-% of silver iodide) of 1.0 g of silver nitrate and an insensitive silver iodobromide emulsion (3 mol-% of silver iodide) of 0.6 g of silver nitrate with 1.0 g of a yellow coupler of the formula:

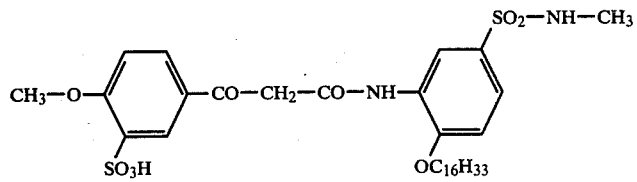

and 2.0 g of gelatine.

9. A covering layer of 0.7 g of gelatine.

Layers 3, 6 and 7 each contain 50 mg of a white coupler of the following formula:

$$\text{C}_{17}\text{H}_{35}-\underset{\underset{\text{N}}{\|}}{\text{C}}\underset{\underset{\displaystyle \underset{\text{SO}_3\text{H}}{\bigcirc}}{|}}{\overset{\text{H}}{-}}\underset{\text{C}=\text{O}}{\overset{|}{\text{C}}}-\text{CH}_3$$

Layer arrangement II

1. The same as layer 1 in the layer arrangement I.
2. An intermediate layer containing 0.7 g of gelatine.
3. The same as layer 4 in layer arrangement I.
4. An intermediate layer containing 0.7 g of gelatine.
5. The same as layer 2 in layer arrangement I.
6. An intermediate layer of 1.0 g of gelatine and a finest grained silver chloride emulsion (Mikrat emulsion, average grain size <0.1 μm) containing 0.17 g of silver nitrate.
7. The same as layer 5 in layer arrangement I.
8. An intermediate layer containing 0.7 g of gelatine.
9. The same as layer 7 in layer arrangement I.
10. The same as layer 8 in layer arrangement I.
11. The same as layer 9 in layer arrangement I.

Layers 2, 4, 6, 8 and 7 contains each 50 mg of the white coupler used in layers 3, 6 and 7 of layer arrangement I.

The materials are hardened with a sulphobetainecarbodiimide of the following formula:

$$\text{CH}_3-\text{N}=\text{C}=\text{N}-(\text{CH}_2)_3-\overset{\oplus}{\underset{\underset{(\text{CH}_2)_4-\text{SO}_3^{\ominus}}{|}}{\text{N}(\text{CH}_2)_3}}$$

(described in German Patent application P 2 625 026.0 under No. V/1).

The emulsifiable DIR compounds are emulsified by the following method:

A solution of 10 g of the DIR compound in 10 g of dibutyl phthalate, 30 ml of ethyl acetoacetate and 5 g of dimethyl formamide is emulsified in a solution of 100 ml of a 5% aqueous gelatine solution and 0.8 g. of a wetting agent, e.g. sulphonated paraffin hydrocarbons, by vigorous mixing in a mixing siren.

The hydrophilic DIR compounds are dissolved in alkali in the usual manner and then adjusted to pH 6.5.

The cast samples were exposed behind a grey continuous wedge to white, red or green light, depending on the purpose of the investigation, and photographically processed as described in "The British Journal of Photography", July 1974, pages 597 and 598.

The γ values were obtained from the colour density curves.

The IIE is defined as follows:

$$IIE = \frac{\gamma s - \gamma w}{\gamma w} \cdot 100\%$$

s = selective exposure
w = white exposure

EXAMPLE 1

Incorporation of the DIR compound in the less sensitive red sensitive layer 1

Layer arrangement: Consisting of layers 1 and 9 of layer arrangement I.
Samples 1–9: Layer 1 contains 80 mg of the DIR compounds indicated in table 1.
Sample 10: No DIR compound in layer 1.

The samples were exposed to red light behind a stepped wedge and developed as indicated above. The gradation (γ) measured is a measure of the efficiency of the DIR compounds, i.e. the lower the gradation, the more powerful the inhibitory action of the DIR compound.

Table 1

| Sample | Compound | $k_{eff}$ | γ |
| --- | --- | --- | --- |
| 1 | 1 | 30 | 1.42 |
| 2 | 10 | 140 | 1.31 |
| 3 | 2 | 1000 | 1.15 |
| 4 | 4 | 1200 | 1.00 |
| 5 | 3 | 1600 | 0.95 |
| 6 | 11 | 1600 | 0.80 |
| 7 | 7 | 3000 | 0.82 |
| 8 | 9 | 5000 | 0.65 |
| 9 | 6 | 10000 | 0.62 |
| 10 | No DIR compound | — | 1.42 |

The effective reaction velocity constants $k_{eff}$ of the emulsions or solutions of the DIR compounds were determined in vitro independently of the test carried out on the layers. The electro chemical method described in German Patent application No. P 2 704 797.8 was used for determining the $k_{eff}$.

In Table 1, the γ-values determined from the practical tests carried out on the DIR compounds in the layer are entered next to the reaction velocity constants $k_{eff}$.

It is clear that the reactivities of the DIR compounds according to the invention cover a wide range, depending on the substitution ($k_{eff}$: 30 to 10000 (1/Mol.sec)). The effect in the layer itself corresponds quite closely to the $k_{eff}$ values apart from minor deviations. The relatively slowly coupling DIR compounds are particularly suitable for use in intermediate layers which contain no other competing couplers.

EXAMPLE 2

| | | IIE % | | Exposure | | | |
| --- | --- | --- | --- | --- | --- | --- | --- |
| | | | | green | red | white | |
| Sample | DIR compounds in layers 1 & 4 | magenta | cyan | magenta γs | cyan γs | magenta$_w$ | cyan$_w$ |
| 1 | 25mg of compound A in layer 1 60mg of compound A in layer 4 | 4 | 15 | 0.95 | 0.98 | 0.91 | 0.85 |

Incorporation of the DIR compound in the less sensitive of the red sensitive and green sensitive layers 1 and 4 in layer arrangement I (layers 1 to 9)

-continued

| | | IIE % | | Exposure | | | |
|---|---|---|---|---|---|---|---|
| | | | | green | red | white | |
| Sample | DIR compounds in layers 1 & 4 | magenta | cyan | magenta $\gamma s$ | cyan $\gamma s$ | magenta$_w$ | cyan$_w$ |
| 2 | 25mg of compound 9 in layer 1 60mg of compound 7 in layer 4 | 25 | 40 | 0.82 | 0.83 | 0.65 | 0.59 |

Incorporation of the DIR compound in the less sensitive of the red sensitive and green sensitive layers 1 and 4 in layer arrangement I (layers 1 to 9)

The magenta IIE and cyan IIE are raised to a much higher level by the DIR compounds according to the invention than by DIR compounds of the acetophenone type.

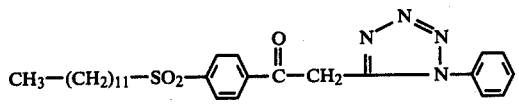

This DIR compound is one of the most highly reactive representatives of the class of acetophenone DIR compounds as described in U.S. Pat. No. 3,632,345.

EXAMPLE 3

Incorporation of the DIR compound into the Mikrat-containing intermediate layer 6 of layer arrangement II.

| | | IIE % | | Exposure | | | |
|---|---|---|---|---|---|---|---|
| | | | | green | red | white | |
| Sample | DIR compound | magenta $\gamma_1/\gamma_2$ | cyan $\gamma_1/\gamma_2$ | magenta $\gamma_{sel}$ $\gamma_1/\gamma_2$ | cyan$\gamma_{sel}$ $\gamma_1/\gamma_2$ | magenta$\gamma_w$ $\gamma_1/\gamma_2$ | cyan$\gamma_w$ $\gamma_1/\gamma_2$ |
| 1 | 25mg of compound 9 in layer 1 60mg of compound 7 in layer 3 100mg of compound A in layer 6 | −8/23 | 2/35 | 0.80/0.89 | 0.73/0.70 | 0.87/0.64 | 0.72/0.52 |
| 2 | 25mg of compound 9 in layer 1 60mg of compound 7 in layer 3 100mg of compound 4 in layer 6 | 20/42 | 25/43 | 0.84/0.95 | 0.70/0.77 | 0.70/0.67 | 0.56/0.54 |

$\gamma_1$ is that gradation section of the characteristic curve which extends from the exposure value corresponding to the sensitivity point (D=0.2 above fog) to an exposure value which is higher by 0.8 log I·t units. The section extending from this end point to an exposure value higher by a further 0.8 log I·t units is referred to as $\gamma_2$.

DIR compound 4 according to the invention increases the magenta IIE and the cyan IIE to a much greater extent than DIR compound A, especially in the $\gamma_1$ region.

We claim:

1. A color photographic material comprising in at least one silver halide emulsion layer or in a light insensitive layer of binder associated therewith, a non-diffusible thioether compound capable of reacting with the oxidation products of a primary aromatic amino color developer substance to release a diffusible silver halide development inhibitor compound, wherein the improvement comprises the non-diffusible thioether compound is a 1,2,5-$\Delta^2$-thiadiazoline-1,1-dioxide which carries in its 4-position a thioether group of the formula —S—X wherein X represents a heterocyclic group which, when split off together with the sulfur atom of the thioether group, forms a diffusible mercapto compound capable of inhibiting the development of the silver halide.

2. A color photographic material as claimed in claim 1, in which the non-diffusible thioether compound corresponds to the following formula I or the corresponding tautomeric form:

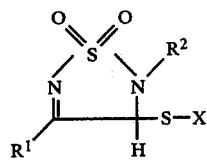

in which
X represents a heterocyclic group which, when split off together with the sulfur atom of the thioether group forms a diffusible mercapto compound capable of inhibiting the development of the silver halide;
$R^1$ represents hydrogen, alkyl, aryl or a heterocyclic group;
$R^2$ represents an acyl group selected from those derived from an aliphatic or aromatic carboxylic acid, a carbonic acid monoester or a N-alkyl- or N-aryl-substituted carbamic acid.

* * * * *